United States Patent [19]

Bühman et al.

[11] Patent Number: 4,973,735
[45] Date of Patent: Nov. 27, 1990

[54] SUBSTITUTED TRIFLUOROETHYL ESTERS OF PHENYLACETIC ACID, PROCESSES FOR THEIR PREPARATION AND THEIR USE AS PESTICIDES

[75] Inventors: Ulrich Bühman; Ortrud Lammer; Hartmut Joppien; Harald von Keyserlingk, all of Berlin, Fed. Rep. of Germany

[73] Assignee: Schering Aktiengesellschaft, Fed. Rep. of Germany

[21] Appl. No.: 402,838

[22] Filed: Sep. 5, 1989

[30] Foreign Application Priority Data

Sep. 2, 1988 [DE] Fed. Rep. of Germany ....... 3830297

[51] Int. Cl.$^5$ .............................................. C07C 69/76
[52] U.S. Cl. ...................................... 560/55; 560/57; 560/14; 560/11; 560/9; 560/20; 560/21; 560/111
[58] Field of Search ...................... 560/111, 55, 57, 14, 560/11, 9, 20, 21; 514/530, 534, 535, 538

[56] References Cited

FOREIGN PATENT DOCUMENTS 3053639  5/1978  Japan .

OTHER PUBLICATIONS

CA 111 (5) 38970n 1989.
CA 98 (13); 106515K 1983.
CA 96 (24)L210105w 1982.
CA 90 (23):186605n 1979.
CA 89 (21):179713x 1978.

*Primary Examiner*—Paul J. Killos
*Attorney, Agent, or Firm*—Ostrolenk, Faber, Gerb & Soffen

[57] ABSTRACT

There are described new trifluoroethyl esters of phenylacetic acid of general formula I

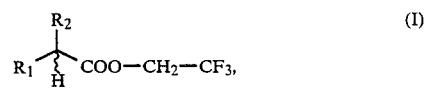

in which $R_1$ and $R_2$ have the meanings given in the description and processes for their preparation. The compounds show insecticidal activity so that they can be used as pesticides.

15 Claims, No Drawings

SUBSTITUTED TRIFLUOROETHYL ESTERS OF PHENYLACETIC ACID, PROCESSES FOR THEIR PREPARATION AND THEIR USE AS PESTICIDES

The invention relates to new trifluoroethyl esters of phenylacetic acid, their preparation and their use as pesticides especially against insects.

It is known that many esters of phenylacetic acid have insecticidal properties, see eg DE No. 32 30 775.

The disadvantage of the known compounds however is that the insecticidal is not sufficiently high.

The object of the present invention is to provide new compounds that combat insects better than compounds known for this purpose.

It has now been found that trifluoroethyl esters of phenylacetic acid of general formula I

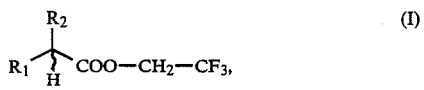

in which
$R_1$ is phenyl, which can be substituted by one or more of the same or different $C_{1-4}$-alkyl, $C_{3-6}$-cycloalkyl, $C_{1-4}$-alkoxy, $C_{2-6}$-alkynyloxy, $C_{2-6}$-alkenyloxy, $C_{3-6}$-cycloalkoxy, $C_{3-6}$-cycloalkylmethoxy, $C_{1-4}$-alkylthio, $C_{1-4}$-alkylsulphinyl, $C_{1-4}$-alkylsulphonyl, phenoxy (each of which group is optionally substituted by halogen), halogen, cyano, nitro or the group $R_3SO_2O$—, in which $R_3$ is $C_{1-4}$-alkyl, $C_{2-4}$-alkenyl, $C_{2-4}$-alkynyl or phenyl, (each of which group is optionally substituted by halogen), and $R_2$ is tertiary butyl or 1-methylcyclopropyl
show better insecticidal activity in comparison with know compounds.

The expression "halogen" in connection with alkyl, cycloalkyl, alkoxy, alkylthio, alkenyl, alkynyl, alkenyloxy, alkynyloxy, cycloalkoxy, cycloalkylmethoxy, phenyl and phenoxy means that one or more hydrogen atoms are replaced by halogen.

The invention covers all isomeric forms and their mixtures of the compounds of formula I.

The trifluoroethyl esters of phenylacetic acid of general formula I of the invention can be prepared in known manner by reacting a phenylacetic acid derivative of general formula II

in which $R_1$ and $R_2$ have the meanings given above and Z is halogen or hydroxy, with 2,2,2-trifluoroethanol.

Reaction of compounds of general formula II, in which Z is halogen is an acylation of an alcohol with a carbonyl chloride (see eg "Reaktionen und Synthesen im organischen Praktikum, L. F. Tietze-Th. Eicher, Thieme Verlag Stuggart, 1981, p 115). The reaction is usually carried out in the presence of an acid acceptor (see for example Houben-Weyl, Methoden der organischen Chemie, Band VIII, p. 541 ff, Georg Thieme Verlag, Stuttgart 1952). Conventional basic materials are suitable as acid acceptors such as aliphatic, aromatic and heterocyclic amines, e.g. triethylamine, dimethylamine, piperidine and pyridine. The reaction can be carried out with or without a solvent. Besides the acid acceptors themselves, suitable solvents or their mixtures include aliphatic and aromatic hydrocarbons which can optionally be chlorinated, such as petroleum ether, benzene, toluene, xylene, dichloromethane, chloroform, carbon tetrachloride, 1,2-dichloroethane, trichloroethylene and chlorobenzene; ethers, such as diethyl and di-n-butyl ether, methyl t-butyl ether, tetrahydrofuran and dioxane; ketones, such as acetone, methyl ethyl ketone, methyl isopropyl ketone and methyl isobutyl ketone; as well as nitriles, such as acetonitrile and propionitrile.

The reactants are usually present in stoichiometric amounts. However an excess of one or more reactants can sometimes be an advantage.

The reaction is generally carried out above 0° C. with sufficient speed. Since the reaction is usually exothermic it is advantageous to cool the reaction vessel.

The reaction of a compound of general formula II, in which Z=hydroxy, with 2,2,2-trifluoroethanol is an esterification of a carboxylic acid (cf. Houben-Weyl, Methoden der organischen Chemie, Band VIII, p. 516 ff, Georg Thieme Verlag, Stuttgart 1952), which can be speeded up in a known way, optionally by addition of catalysts, such as sulphuric acid, hydrogen halides or sulphonic acids or acid ion exchange resins, and the esterification equilibrium can be pushed into the desired direction by removal, from the reaction mixture, the water or the ester of general formula I, such as for example by azeotropic distillation.

The compounds of the invention can be also be synthesised by practically all the conventional methods for esters, eg using a carboxylic acid anhydride derived from the carboxylic acid of formula II, or by treatment of salts of this carboxylic acid with 2,2,2-trifluoroethyl iodide or other reactive derivatives of 2,2,2-trifluoroethanol such as its mesylate or tosylate. Preferred salts of these carboxylic acids are alkali metal salts, such as lithium, sodium or potassium salts, or alkaline earth metal or ammonium salts, eg calcium or triethylammonium salt.

The phenylacetic acids of general formula II in which Z is H are partially known compounds. They can be prepared by known methods (see eg J. Org. Chem. 32 (9) 1967, 2799 and 2801 and Chem. Ber. 116 (1983) 3708–3724).

Phenylacetyl chlorides of general formula II, in which Z is Cl, can be prepared by known methods.

The compounds of the invention prepared by the above described processes can be isolated from the reaction mixture in conventional manner, for example by distillation of solvent, at normal or reduced pressure, by precipitation with water or by extraction.

A higher degree of purity can be achieved as general rule by column layer chromatography purification or by fractional distillation.

The compounds of the invention are, as a rule, almost colourless and liquids that are almost insoluble in water, highly soluble in aliphatic hydrocarbons, such as petroleum ether, hexane, pentane and cyclohexane, in chlorinated hydrocarbons, such as chloroform, methylene dichloride and carbon tetrachloride, aromatic hydrocarbons such as benzene, toluene and xylene, ethers, such as diethyl ether, tetrahydrofuran and dioxane, nitriles, such as acetonitrile, alcohols, such as methanol and ethanol, amides, such as dimethylformamide, and sulphoxides, such as dimethyl sulphoxide.

The compounds of the invention are distinguished by good insecticidal activity thus represent a valuable improvement in the state of the art. Based on their activity against a wide range of sucking arthropods, the compounds of the invention can be used not only against pests in crops but also for combating human and domestic animal parasites. The activity of the compounds of the invention is of particular importance against parasites which have developed resistance to other substances. Since the compounds of the invention are taken up by the plants and transported systemically, they can also be applied to the soil and thus reach those plant parts that cannot be treated directly.

Examples of insects, including animal ectoparasites, that can be combated by the compounds of the invention include Lepidoptera, such as *Plutella xylostella, Spodoptera littoralis, Heliothis armigera* and *Pieris brassicae*; Diptera, such as *Musca domestica, Ceratitis capitata, Erioischia brassicae, Lucilia sericata* and *Aedes aegypti*; Homoptera, including aphids such as *Megoura viciae* and *Nilaparvata lugens*; Coleoptera, such as *Phaedon cochleariae, Anthonomus grandis* and corn rootworms (*Diabrotica* spp. eg. *Diabrotica undecimpunctata*); Orthoptera, such as *Blattella germanica*; and lice, such as *Damalinia bovis* and *Linognathus vituli*.

The compounds according to the invention can be used at a concentration of 0.0005 to 5%, preferably from 0.001 to 1%, calculated as gram active material per 100 ml of the composition.

The compounds of the invention can be used either alone or in mixture with each other or another insecticide. Optionally other plant protection or pesticidal compositions, such as for example insecticides, acaricides or fungicides can be added depending on the desired result.

An improvement in the intensity and speed of action can be obtained, for example, by addition of suitable adjuvants, such as organic solvents, wetting agents and oils. Such additives may allow a decrease in the dose.

Suitable mixture partners may also include phospholipids, e.g. such as from the group phosphatidylcholine, hydrogenated phosphatidylcholine, phosphatidylethanolamine, N-acyl-phosphatidylethanolamine, phosphatidylinositol, phosphatidylserine, lysolecithin or phosphatidylglycerol.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons such as benzene, toluene, xylene, cyclohexanone, isophorone, dimethyl sulphoxide, dimethylformamide, other mineral-oil fractions and plant oils.

Suitable solid carriers include mineral earths, e.g. tonsil, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts, Formulations can be prepared, for example, from the following ingredients.

A. WETTABLE POWDER 20 percent by weight active ingredient
35 percent by weight bentonite
8 percent by weight calcium lignosulphonate
2 percent by weight of the sodium salt of N-methyl-N-oleyltaurine
35 percent by weight silicic acid

B. PASTE 45 percent by weight active ingredient
5 percent by weight sodium aluminium silicate
15 percent by weight cetylpolyglycol ether with 8 moles ethylene oxide
2 percent by weight spindle oil
10 percent by weight polyethylene glycol
23 parts water

C. EMULSIFIABLE CONCENTRATE 20 percent by weight active ingredient
75 percent by weight isophorone
5 percent by weight of a mixture based on the sodium salt of N-methyl-N-oleyltaurine and calcium lignosulphonate The following Examples illustrate the preparation of compounds of the invention.

EXAMPLE 1

2,2,2-Trifluoroethyl 2-(4-ethoxy-3-fluorophenyl)-3,3-dimethylbutyrate 3.0 g (0.011 mol) 2-(4-Ethoxy-3-fluorophenyl)-3,3-dimethylbutyryl chloride was added dropwise to a solution of 1.12 g (0.0121 mol) 2,2,2-trifluoroethanol and 100 mg 4-dimethylaminopyridine in 15 ml pyridine at 0° C. After stirring for two hours at room temperature, tlc showed complete reaction. The mixture was added to ice/water, made weakly acidic, extracted with ether, the extract dried over magnesium sulphate and evaporated under reduced pressure. After silica gel chromatography, 2.80 g (=75.6% of theory) of a pale yellow oil was obtained. $n_D^{20}$: 1.4783

In a similar manner, the following compounds were prepared.

| Example No. | $X_1$ | $X_2$ | $n_D^{20}$ |
|---|---|---|---|
| 2 | —OEt | H | 1,4641 |
| 3 | —Cl | H | 1,4707 |
| 4 | —OMe | F | 1,4554 |
| 5 | —OMe | H | 1,4619 |
| 6 | —OCF$_3$ | H | 1,4244 |
| 7 | —OCH$_3$ | Cl | 1,4826 |
| 8 | —OEt | Cl | 1,4778 |
| 9 | —Et | H | 1,4574 |
| 10 | H | H | 1,4539 |
| 11 | —CF$_3$ | H | 1,4296 |

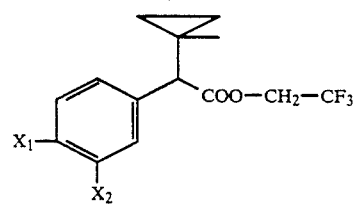

-continued

| Example No. | X₁ | X₂ | $n_D^{20}$ |
| --- | --- | --- | --- |
| 12 | —OEt | H | 1,4741 |
| 13 | —OEt | F | 1,4664 |

Use Example A

Activity against eggs/larvae of the corn rootworm (*Diabrotica undecimpunctata*)

The compounds of the invention were made up as aqueous emulsions at a concentration of 0.1%. The soil in polystyrene petri dishes, containing maize seedlings (1 seedling/dish) and ca. 50 eggs of the corn rootworm (*Diabrotica undecimpunctata*) were sprayed with these preparations (4 mg spray/cm²). The closed dishes were left at 25° C. under extended daylight conditions for 4 days. The criterion for judging the activity was the death of eggs or newly hatched larvae at the end of the test.

The compounds of Examples 1, 2, 4 and 5 showed 80–100% activity.

Use Example B

Soil insecticide activity against eggs/larvae of the corn rootworm (*Diabrotica undecimpunctata*)

Formulations of compounds of the invention were made up with an active ingredient content of 0.1%. 5 ml of this preparation was pipetted into 300 ml clear plastic beakers, containing 50 cm³ earth and ca. 50 Diabrotica eggs as well as 2 presoaked of maize seeds. The sealed pots were left for 10 days under extended daylight conditions at 25° C. The criterion for judging the activity after 10 days was the larvicidal activity and the root growth of the emerging maize plants in the treated pots in comparison with untreated controls.

It was shown that compounds of Examples 1–4 gave 90–100% larvicidal activity and allowed good root growth.

Use Example C

Activity in prophylactic treatment of leaves against brown rice-hoppers (*Niliparvata lugens Stal*)

Rice seedlings (about 15 per pot) were grown in a warm glasshouse, until formation of the third leaf and then sprayed, until dripping wet, with an aqueous preparation containing 0.1% of active material. After drying the sprayed leaves, a transparent cylinder was placed over each pot. 30 Adult brown rice-hoppers (*Niliparvata lugens*) were introduced into each pot. After 2 days at 26° C. in the glasshouse, the amount of dead hoppers was determined. The activity was calculated using to Abbott's method in comparison with a few untreated remaining control pots.

The compounds of Examples 1–5 and 10–13 had an activity of 80–100%.

Use Example D

Activity in the curative treatment of broad beans (*Vicia fabae* L.) against black bean aphids (*Aphis fabae scop.*)

Seedlings of broad beans (*Vicia fabae*), one plant per pot, were grown in a warm glasshouse, to a height of about 6 cm. The plants were then covered with a culture of black bean aphid (*Aphis fabae*). After each plant had been colonised with 100 to 200 insects, they were each sprayed with an aqueous preparation of each respective active ingredient at a concentration of 0.1%, until dripping wet, and left in the glasshouse at about 24° C. After 2 days the amount of dead aphids was ascertained. The activity was calculated using to Abbott's method in comparison with a untreated remaining control pots.

The compound of Example 1 had an activity of greater than 80%.

Use Example E

Activity against Sheep blowfly (*Lucilia sericata*)

1 ml aliquots of acetone solutions or suspensions, containing test compound at various concentrations, were applied to cotton wool dental rolls (1 cm×2 cm), contained in glass vials 2 cm diameter×5 cm long. After drying, the treated materials were then impregnated with 1 ml of nutrient solution, infested with approximately 30 first instar larvae of sheep blow fly (*Lucilia sericata*), closed by a cotton wool plug and held at 25° C. for 24 hours. For the controls the mortality was <5% whereas compounds of Examples 1, 4, 5, and 13 had an $LC_{50}$ of less than 300 ppm.

Use Example F

Activity against house fly (*Musca domestica*)

Aliquots (0.7 ml) of acetone solutions or suspensions of test compounds at various concentrations were applied to filter papers (9 cm diameter) placed in the bottom of petri dishes (9 cm diameter) closed by glass lids. After evaporation of solvent, the treated surfaces, together with controls treated with acetone alone, were then infested with adult houseflies, (*Musca domestica*) and held at 22° C. for 24 hours. The percentage mortality of the insects was then recorded. Less than 5% mortality resulted in the controls whereas the $LD_{50}$ of compounds of Examples 1, 3, 4, 5, 7, 10 and 13 was less than 1000 mg/m².

We claim:

1. Substituted trifluoroethyl esters of phenylacetic acid of general formula I

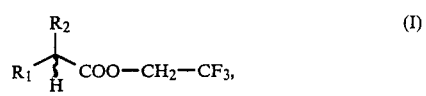

in which

R₁ is phenyl, which can be substituted by one or more of the same or different $C_{1-4}$-alkyl, $C_{3-6}$-cycloalkyl, $C_{1-4}$-alkoxy, $C_{2-6}$-alkynyloxy, $C_{2-6}$-alkenyloxy, $C_{3-6}$-cycloalkoxy, $C_{3-6}$-cycloalkylmethoxy, $C_{1-4}$-alkylthio, $C_{1-4}$-alkylsulphinyl, $C_{1-4}$-alkylsulphonyl, phenoxy (each of which group is optionally substituted by halogen), halogen, cyano, nitro or the group $R_3SO_2O$—, in which $R_3$ is $C_{1-4}$-alkyl, $C_{2-4}$-alkenyl, $C_{2-4}$-alkynyl or phenyl, (each of which group is optionally substituted by halogen), and R₂ is tertiary butyl or 1-methylcyclopropyl 2. An insecticidal composition which comprises a compound claimed in claim 1, in admixture with an agriculturally acceptable diluent or carrier.

3. A method of combating insects, which comprises applying to the insect or its locus an effective amount of a compound claimed in claim 1.

4. Substituted triphenylethyl ether of phenylacetic acid according to claim 1 in which R₁ is phenyl or phenyl which is mono-substituted or di-substituted by alkoxy, fluoroalkyl or halogen.

5. Substituted triphenylethyl ester of phenylacetic acid according to claim 4 in which $R_1$ is substituted at the 4 position by methoxy, ethoxy, trifluoromethyl or chloro and the 3 position is unsubstituted or substituted by halogen and $R_2$ is tertiary butyl.

6. Substituted trifluoroethyl ether of phenylacetic acid according to claim 5 in which $R_1$ is phenyl substituted at the 4 position by methoxy or ethoxy and the 3 position is unsubstituted or substituted by fluoro.

7. Substituted trifluoroethyl ether of phenylacetic acid according to claim 4 in which $R_1$ is substituted at the 4 position by ethoxy and the 3 position is unsubstituted or substituted by fluoro and in which $R_2$ is 1-methylcyclopropyl.

8. An insecticidal composition which comprises a compound claimed in claim 4, in admixture with an agriculturally acceptable diluent or carrier.

9. An insecticidal composition which comprises a compound claimed in claim 5, in admixture with an agriculturally acceptable diluent or carrier.

10. An insecticidal composition which comprises a compound claimed in claim 6, in admixture with an agriculturally acceptable diluent or carrier.

11. An insecticidal composition which comprises a compound claimed in claim 7, in admixture with an agriculturally acceptable diluent or carrier.

12. A method of combating insects, which comprises applying to the insect or its locus an effective amount of a compound claimed in claim 4.

13. A method of combating insects, which comprises applying to the insect or its locus an effective amount of a compound claimed in claim 5.

14. A method of combating insects, which comprises applying to the insect or its locus an effective amount of a compound claimed in claim 6.

15. A method of combating insects, which comprises applying to the insect or its locus an effective amount of a compound claimed in claim 7.

* * * * *